(12) United States Patent
Irvin et al.

(10) Patent No.: US 7,402,679 B1
(45) Date of Patent: *Jul. 22, 2008

(54) ONE-POT PROCESS FOR MAKING MULTIFUNCTIONAL TETRAZOLE POLYOLS TO PRODUCE TETRAZOLE BASED POLYMERS

(75) Inventors: David J. Irvin, Ridgecrest, CA (US); Mark H. Mason, Inyokern, CA (US); Stephen Fallis, Ridgecrest, CA (US); Andrew Chafin, Ridgecrest, CA (US); Richard Hollins, Ridgecrest, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 458 days.

This patent is subject to a terminal disclaimer.

(21) Appl. No.: 11/151,178

(22) Filed: May 27, 2005

(51) Int. Cl.
*C07D 257/04* (2006.01)
(52) U.S. Cl. ..................................... 548/250
(58) Field of Classification Search ................. 514/381; 548/250
See application file for complete search history.

(56) References Cited

OTHER PUBLICATIONS

Copending U.S. Appl. No. 11/151,180 (same applicant).*
National Institute of Standards and Technology 1H-Tetrazole data sheet, Feb. 26, 2008, 1 pg, http://webbook.nist.gov/chemisrty.

* cited by examiner

*Primary Examiner*—Kamal Saeed
*Assistant Examiner*—Susannah Chung
(74) *Attorney, Agent, or Firm*—Brian F. Drazich; Charlene A. Haley

(57) ABSTRACT

A process for making energetic urethane cured binders by making poly-tetrazoles to produce multi-functional tetrazole polyols for producing tetrazole base polymers. Embodiments of the present invention relate generally to a process for preparation of a monomer including reacting an effective amount of nitrile(s) with inorganic azide and a divalent zinc salt in a first solvent, cooling to room temperature producing poly tetrazole purifying the poly tetrazole by recrystallization or precipitation in a second solvent, and reacting an effective amount of the purified poly-tetrazole with a third solvent, a soluble reversible or non-reversible base, and 2-chloro-ethanol, cooling to room temperature producing tetrazole polyol. Embodiments of the present invention further include the monomers produced by the processes described herein.

17 Claims, No Drawings

ONE-POT PROCESS FOR MAKING MULTIFUNCTIONAL TETRAZOLE POLYOLS TO PRODUCE TETRAZOLE BASED POLYMERS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

There is a need for novel energetic binders to increase the performance of pyrotechnics, gun propellants, rocket propellants, air-bag gas generator propellants, and explosives. Depending on the application, these materials are typically 3-25% binder by mass. Therefore, improvements to the energy content, mechanical properties, or insensitive munitions properties of the polymeric binder can have significant affects on the performance of the energetic material in question.

In general many pyrotechnics, propellants, explosives are comprised of a polymeric binder that holds one or more energetic solids in a plastic matrix. The polymeric binder serves many roles in these materials. Initially the polymer can aid in processing. In fact, the properties of the polymer will significantly affect how a material is processed, whether it is cast or pressed or extruded. Furthermore, the polymer mechanically holds all the ingredients together, serving as a structural element literally binding together the final material. This role is especially critical in rocket propellants, because cracks and voids in the propellant will lead to motor grain failure, often with catastrophic results. The binder serves many safety functions. The binder physically coats the energetic solids in these materials, this provides a physical buffer to minimize the physical and chemical interaction of reactive solids with each other. This generally lowers the electrostatic discharge, impact, and friction sensitivity of the final material. In some materials, especially rocket propellants, the binder also serves as a fuel when the hydrocarbon polymer is combusted by the oxidizer. However, the binder generally diminishes the performance (detonation pressure and velocity) of most explosives. To improve the performance of explosives with significant binder content, and to increase the energy density of propellants energetic polymers are needed.

While there are energetic binders available (polyglycidyl nitrate (PGN), polyglycidyl azide (GAP), azidomethyl-methyl-oxetane (AMMO), bis((azido-methyl)oxetane) (BAMMO), nitratomethyl-methyloxetane (NMMO), etc.) the safety benefits of increasing binder content are lost because these materials contain either organic azides or nitrate esters (or both). These functional groups are chemically unstable, easily ignited, and generally create reactive fragments on aging. In fact, propellants that utilize nitrate esters generally require expensive monitoring programs throughout their life cycle to insure both adequate safety properties and performance as the propellant ages. The cost of such monitoring is often cited as one reason most modern explosives do not to use nitrate esters as binder materials. Furthermore, the energetic groups are pendant moieties attached to the polymer, but not incorporated into the polymer backbone. This impairs the physical properties of these polymers and causes the formulator to need a higher weight percent of binder in order to achieve adequate coating. In short, there is a need for improved energetic binders to address safety, performance, aging, and processing requirements.

While tetrazoles are somewhat less energetic than azides or nitrates, the bis-alkyltetrazoles of interest are more thermally stable and substantially less chemically reactive. Higher percentages of these binders could be used without anticipating negative safety consequences. Furthermore, the energetic functionality is built into the polymer backbone, minimizing the total moles of pendant atoms. This is anticipated to yield a binder with superior physical properties. A dihydroxy-terminated bis-tetrazole (2,2 Bis((2-ethanol)-1 or 2H-tetrazole)-propane or BETP) has been synthesized on the multigram scale. Initial differential scanning calorimetery (DSC) analysis shows this pre-polymer has promise as an energetic cured urethane binder for explosives and propellants and gas generatos.

U.S. Pat. No. 5,053,086 issued on Oct. 1, 1991 to Henry, et al., which teaches gas generating compositions containing energetic high nitrogen such as ammonium 5-nitraminotetrazole and 5,5'-bitetrazole. This work yielded polymeric binders that are too rigid and "glassy" for the intended application. The chemical structure of the present invention polymers builds more flexibility into the backbone, yielding improved elastomers. Further research by Demko teaches the addition of sodium azide to nitrites to give 1H-tetrazoles in water with zinc salts as catalysts. (Demko, Z. P.; Sharpless, K. B. "Preparation of 5-substituted 1H-tetrazoles from nitrites in water." *J. Org. Chem.* 2001, 66, 7945). This step is only one method to obtain the tetrazole intermediate. Further reaction is necessary to produce the alcohol-based monomers. The addition of the alkyl alcohol is two fold: first, the short alkyl chain adds flexibility, solubility; second, the alcohol group allows for the production of stable polyurethanes. Polymerization of the tetrazole would produce the less stable polyurea.

Tetrazole compounds have application in many fields including, but not limited to, chemistry, ligands, metabolically stable surrogate for a carboxylic acid group, and material sciences including explosives and propellants and air bag gas generators.

It is to be understood that the foregoing general description and the following detailed description are exemplary and explanatory only and are not to be viewed as being restrictive of the present invention, as claimed. Further advantages of this invention will be apparent after a review of the following detailed description of the disclosed embodiments and in the appended claims.

DETAILED DESCRIPTION OF THE INVENTION

Embodiments of the present invention generally relate to a process for preparation of a monomer having the general structure (I) comprising: reacting an effective amount of nitrile(s) with

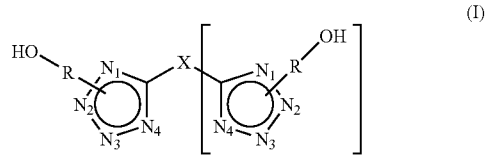

inorganic azide and a divalent zinc salt in a first solvent at a temperature in the range of about 70° C. to about 170° C. for a time period in the range of about 1 to 24 hours, wherein [n] of said nitrile(s) is 2-9, wherein [X] comprises at least one group of alkyls, aryls, and oligoethers, wherein said nitrile(s) having the general structure (II); cooling to room temperature producing poly tetrazole having the general structure (III), wherein [H] is chemically bonded to $N_1$ or $N_2$ position, wherein [X]

(II)

comprises at least one group of alkyls, aryls, and oligoethers, wherein [n] is a value of 2 to 9; purifying the poly tetrazole by recrystallization or precipitation in a second solvent; reacting

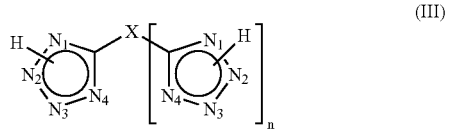

(III)

an effective amount of the purified poly tetrazole with a third solvent, a soluble reversible or non-reversible base, and 2-chloro-ethanol at a temperature in the range of about 70° C. to about 150° C. for a time period in the range of about 1 to about 24 hours, cooling to room temperature producing tetrazole polyol having the general structure (I), wherein [R] comprises at least one group of alkyls, aryls, and oligoethers, wherein [R] is chemically bonded to $N_1$ or $N_2$ position, wherein [X] comprises at least one group of alkyls, aryls, and oligoethers, wherein [n] is a value of 2 to 9; and wherein the structure (I) is prepared in a one-pot process. Embodiments of the present invention further include the monomers produced by the processes described herein.

When the process utilizes nitrile(s), the nitrile(s) include, but not limited to, at least one of tricyanomethane, tetracyanopropane, pentacyanopropane, and hexacyanopropane. When tetracyanopropane is utilized it includes at least 1,1,3,3-tetracyanopropane. The poly tetrazole produced includes at least one of tri-tetrazole, tetra-tetrazole, penta-tetrazole, hexa-tetrazole, hepta-tetrazole, septa-tetrazole, octa-tetrazole, nona-tetrazole, and deca-tetrazole.

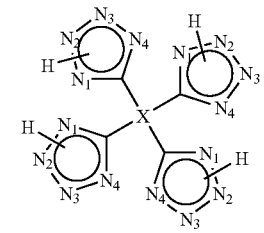

General Structure of tetrafunctional tetrazole

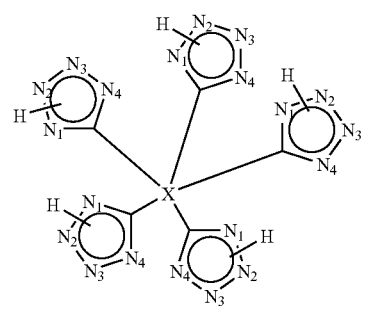

General Structure of pentafunctional tetrazole

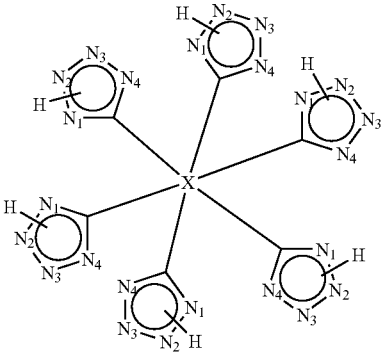

General Structure of hexafunctional tetrazole

In other embodiments, the tetrazole polyol produced includes at least one of tri-tetrazole polyol, tetra-tetrazole polyol, penta-tetrazole polyol, hexa-tetrazole, hepta-tetrazole, septa-tetrazole, octa-tetrazole, nona-tetrazole, and deca-tetrazole.

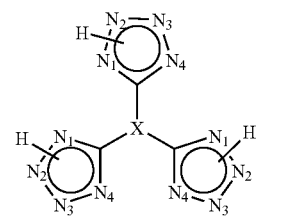

General Structure of trifunctional tetrazole

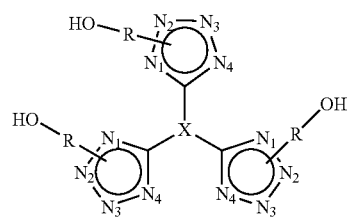

General structure of trifunctional monomer

-continued

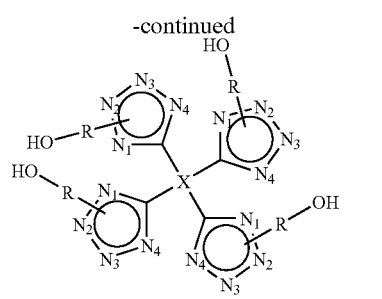

General structure of tetrafunctional monomer

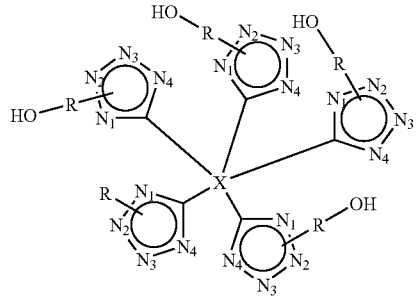

General structure of pentafunctional monomer

In embodiments, the inorganic azide includes at least one of sodium azide, lithium azide, and potassium azide. In the process for making tetrazole diols, the divalent salts utilized include, but not limited to, at least zinc bromide. The first solvent is polar which includes at least one of water, alcohol including 2-propanol, dimethylformanide, dimethylacetamide, and N-methyl pyrrolidinone. The second solvent includes at least one of ethyl acetate and hexane. The third solvent is polar which includes at least one of water, alcohol including 2-propanol, dimethylformanide, dimethylacetamide, and N-methylpyrrolidinone. In embodiments of the present invention, a soluble base is utilized. The soluble reversible base includes at least one of sodium hydroxide, lithium hydroxide, and potassium hydroxide. The soluble non-reversible base includes at least one of sodium hydride, lithium hydride, and potassium hydride.

The poly tetrazoles produced includes at least one of tri-tetrazole, tetra-tetrazole, penta-tetrazole, hexa-tetrazole, hepta-tetrazole, septa-tetrazole, octa-tetrazole, nona-tetrazole, and deca-tetrazole. In embodiments of the present invention, the tetrazole polyol includes its isomer and each tetrazole polyol isomer is independent of other tetrazole polyol isomers. In embodiments of the present invention, the tetrazole polyol is alkylated tetrazole polyol and each alkylated tetrazole polyol includes its isomer and each alkylated tetrazole polyol isomer is independent of other alkylated tetrazole polyol isomers. Depending on the alkylated poly tetrazole utilizes, the alkylated tetrazole polyol isomer produced is alkylated tetra-tetrazole polyol or alkylated tri-tetrazole polyol. In other embodiments, the tetrazole polyol is arylated tetrazole polyol, and the arylated tetrazole polyol includes its isomer and each arylated tetrazole polyol isomer is independent of other arylated tetrazole polyol isomers. Depending on the arylated poly tetrazole utilized, the arylated tetrazole polyol isomer is arylated tetra-tetrazole polyol or tri-tetrazole polyol or any other larger tetrazole polyol.

Experimental Result

In the making of tris-(hydroxyethyl-5-tetrazoyl)methane, the following is formulated. To a suspension of 1.05 gms tris-5-tetrazoylmethane (4.8 mmoles) in 25 mL water was added 0.67 gms NaOH (16.8 mmoles). This was heated to just below reflux at which time 1.0 mL 2-chloroethanol (15 mmoles) was added. The solution was refluxed overnight then cooled and concentrated in vacuum. 20 mL EtOAc was added to the residue. MeOH was then added dropwise until the gummy residue dissolves. The solids are filtered off and the filtrate was concentrated in vacuum to give 1.41 grams of a brown glass. This was taken up in 50 mL 10% MeOH/CHCl$_3$ and poured onto a short column of Silica Gel. The product was eluted using 50% MeOH/CHCl$_3$ to give 0.69 gms of a straw colored glass.

The following is an example of a one-pot process for making multifunctional monomers (1,1,3,3-tetra(hydroxyethyl-5-tetrazolyl)propane). Sodium azide (31.4 g) and zinc bromide (97.5 g) were dissolved in DMAc (500 mL) (Caution: exothermic) After cooling to below 50° C., the 1,1,3,3 tetracyanopropane was added, and the mixture was heated to 100° C. After 24 hours, 2-chloroethanol (44 mL) and sodium hydroxide (4 eq to tetracyanopropane) were added. The solution was heated to 100° C. for an addition 24 hours. The DMAc was distilled off at 100° C. under full vacuum. (Caution: do not over heat) The resulting dark brown viscous liquid was diluted with acetone to precipitate salts. The solution was charcoal treated and filtered to yield a pale solution. The acetone was removed via reduced pressure distillation to yield a light brown gum. The material was dried in a vacuum oven at 100° C. for 96 hours to yield 55 g of a brown solid.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:
1. A process for preparation of a compound of structure (I) comprising:

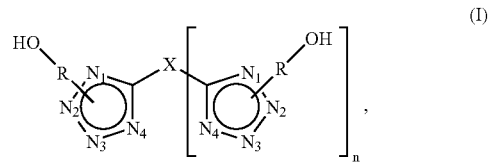

wherein "n" is 2-9 and "X" is a group consisting of at least one of alkyl, aryl, and oligoether, reacting in a first solvent an inorganic azide and a divalent zinc salt with a nitrile having the general structure (II), where "n" of said nitrile has a value of 2 to 9, at a temperature in the range from about 70° C. to about 170° C. for a time period in the range from about 1 hour to about 24 hours, allowing contact of reactants, "X" is a group consisting of at least one of alkyl, aryl, and oligoether, to form a first composition;

cooling said first composition to about room temperature to form a second composition including poly tetrazole having the general structure (III), wherein "n" has a value of 2 to 9, and "H" is chemically bonded to $N_1$ or $N_2$;

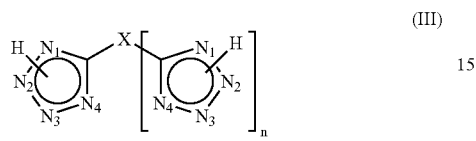

isolating said poly tetrazole by recrystallization or precipitation from a suitable second solvent;

reacting said poly tetrazole in a third solvent with a soluble reversible or non-reversible base and 2-chloro-ethanol at a temperature in the range from about 70° C. to about 150° C. for a time period in the range from about 1 hour to about 24 hours, allowing contact of reactants, to form a third composition;

cooling said third composition to about room temperature to form a fourth composition including tetrazole polyol having the general structure (I), wherein "R" is a group consisting of at least one of alkyl, aryl, and oligoether, and "R" is chemically bonded to $N_1$ or $N_2$; and wherein said structure (I) is prepared in a one-pot process.

2. The process according to claim 1, wherein said poly tetrazole is at least one of tri-tetrazole, tetra-tetrazole, penta-tetrazole, and hexa-tetrazole.

3. The process according to claim 1, wherein said tetrazole polyol is at least one of tri-tetrazole polyol, tetra-tetrazole polyol, penta-tetrazole polyol, and hexa-tetrazole polyol.

4. The process according to claim 1, wherein said inorganic azide is at least one sodium azide, lithium azide, and potassium azide.

5. The process according to claim 1, wherein said divalent zinc salt is zinc bromide.

6. The process according to claim 1, wherein said first solvent is a polar solvent at least one of which is selected from the group of polar solvents consisting of water, alcohol, 2-propanol, dimethylformanide, dimethylacetamide, and N-methylpyrrolidinone.

7. The process according to claim 1, wherein said second solvent is at least one of ethyl acetate and hexane.

8. The process according to claim 1, wherein said third solvent is a polar solvent at least one of which is selected from the group of polar solvents consisting of water, alcohol, 2-propanol, dimethylformanide, dimethylacetamide, and N-methylpyrrolidinone.

9. The process according to claim 1, wherein said soluble reversible base is at least one of sodium hydroxide, lithium hydroxide, and potassium hydroxide.

10. The process according to claim 1, wherein said soluble non-reversible base is at least one of sodium hydride, lithium hydride, and potassium hydride.

11. The process according to claim 1, wherein said tetrazole polyol is alkylated tetrazole polyol.

12. The process according to claim 1, wherein said tetrazole polyol is arylated tetrazole polyol.

13. The process according to claim 1, wherein said nitrile is at least one of tricyanomethane, tetracyanopropane, pentacyanopropane, and hexacyanopropane.

14. The process according to claim 1, wherein said tetracyanopropane is 1,1,3,3-tetracyanopropane.

15. The monomer produced by the process of claim 1 having the general structure (I).

16. A process for preparation of a compound of structure (I) comprising:

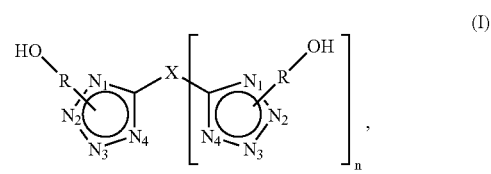

wherein "n" is 2-9 and "X" is a group consisting of at least one of alkyl, aryl, and oligoether, reacting, in a vessel, dimethylacetamide solvent, an inorganic azide, and a divalent zinc salt with a nitrile having the general structure (II),

where "n" of said nitrile has a value of 2 to 9 and "X" is a group consisting of at least one of alkyl, aryl, and oligoether, at a temperature in the range from about 70° C. to about 170° C. for a time period in the range from about 1 hour to about 24 hours, allowing contact of reactants, to form a first composition including the poly tetrazole having the general structure (III), wherein "n" has a value of 2 to 9, and "H" is chemically bonded to $N_1$ or $N_2$

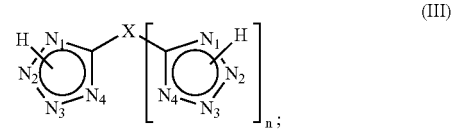

adding 2-chloroethanol and an inorganic base to said vessel to form a second composition;

incubating said second composition at a temperature in the range from about 70° C. to about 150° C. for a time period in the range from about 1 hour to about 24 hours, allowing contact of reactants in said vessel, to form a third composition;

distilling said third composition at about 100° C. under low pressure to remove said dimethylacetamide from said vessel to form a fourth composition;

adding acetone to said fourth composition in said vessel to form a fifth composition including a precipitate;

distilling said fifth composition under low pressure to remove said acetone from said vessel to form a sixth composition including the tetrazole polyol having the general structure (I), where "n" of said polyol has a value of 2 to 9, and "R" is a group consisting of at least one of alkyl, aryl, and oligoether, that is chemically bonded to $N_1$ or $N_2$.

17. A process for preparation of a compound of structure (I) comprising:

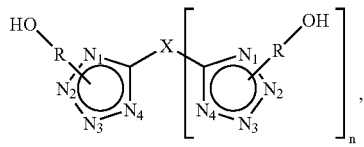
(I)

wherein "n" is 2-9 and "X" is a group consisting of at least one of alkyl, aryl, and oligoether, reacting, in a vessel, dimethylacetamide solvent, an inorganic azide, and a divalent zinc salt with the nitrile 1,1,3,3-tetracyanopropane having the general structure (II),

(II)

where "n" of said nitrile has a value of 3 and "X" is propane, at a temperature in the range from about 70° C. to about 170° C. for a time period in the range from about 1 hour to about 24 hours, allowing contact of reactants, to form a first composition including the poly tetrazole having the general structure (III), wherein "n" has a value of 3, and "H" is chemically bonded to $N_1$ or $N_2$

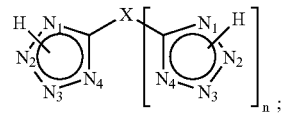
(III)

adding 2-chloroethanol and an inorganic base to said vessel to form a second composition;

incubating said second composition at a temperature in the range from about 70° C. to about 150° C. for a time period in the range from about 1 hour to about 24 hours, allowing contact of reactants in said vessel, to form a third composition;

distilling said third composition at about 100° C. under low pressure to remove said dimethylacetamide from said vessel to form a fourth composition;

adding acetone to said fourth composition in said vessel to form a fifth composition including a precipitate;

distilling said fifth composition under low pressure to remove said acetone from said vessel to form a sixth composition including the tetra-tetrazole polyol having the general structure (I), where "n" of said polyol has a value of 3 and "R" is a group consisting of at least one of alkyl, aryl, and oligoether, that is chemically bonded to $N_1$ or $N_2$.

* * * * *